United States Patent
Ebelsberger et al.

(10) Patent No.: US 9,791,426 B2
(45) Date of Patent: Oct. 17, 2017

(54) SENSOR APPARATUS FOR ANALYZING A GAS MIXTURE IN A PROCESS CHAMBER

(71) Applicant: SIEMENS AKTIENGESELLSCHAFT, München (DE)

(72) Inventors: Gerit Ebelsberger, München (DE); Holger Hackstein, Dietzenbach (DE); Erhard Magori, Feldkirchen (DE)

(73) Assignee: SIEMENS AKTIENGESELLSCHAFT (DE)

( * ) Notice: Subject to any disclaimer, the term of this patent is extended or adjusted under 35 U.S.C. 154(b) by 293 days.

(21) Appl. No.: 14/749,682

(22) Filed: Jun. 25, 2015

(65) Prior Publication Data
US 2016/0003789 A1    Jan. 7, 2016

(30) Foreign Application Priority Data
Jul. 2, 2014    (DE) .................... 20 2014 005 420 U

(51) Int. Cl.
*G01N 33/00*    (2006.01)
*G01N 1/22*    (2006.01)
*F23R 3/00*    (2006.01)

(52) U.S. Cl.
CPC ........... *G01N 33/004* (2013.01); *F23R 3/002* (2013.01); *G01N 1/2226* (2013.01); *G01N 1/2247* (2013.01)

(58) Field of Classification Search
CPC .. G01N 33/004; G01N 1/2226; G01N 1/2247; F23R 3/002
See application file for complete search history.

(56) References Cited

U.S. PATENT DOCUMENTS

| | | | | |
|---|---|---|---|---|
| 4,339,318 A | * | 7/1982 | Tanaka | G01N 27/4077 204/408 |
| 4,736,618 A | * | 4/1988 | Usami | G01N 33/0016 73/31.05 |
| 5,423,228 A | * | 6/1995 | Budd | G01N 1/2258 73/863.21 |
| 6,015,533 A | | 1/2000 | Adams | |

(Continued)

FOREIGN PATENT DOCUMENTS

| AT | 1571 U1 | 7/1997 |
|---|---|---|
| DE | 19916797 A1 | 11/2000 |

(Continued)

*Primary Examiner* — John Fitzgerald
(74) *Attorney, Agent, or Firm* — Schmeiser Olsen & Watts LLP

(57) ABSTRACT

A sensor apparatus for analyzing a gas in a process chamber, having a housing, a gas sensor for analyzing at least a part of the gas, the gas sensor being arranged at a determined position in the housing, a gas feed for connecting the housing to the process chamber to feed the part of the gas from the process chamber into the housing and to the determined position, and a gas discharge for discharging the gas from the housing, wherein the gas feed and the gas discharge are configured as tubes lying inside one another, characterized by a closure cap at the combustion chamber-side end of the tubes lying inside one another, the closure cap including an even number of at least four openings with the same area, which are connected alternately as a gas inlet and a gas outlet to the tubes lying inside one another is provided.

12 Claims, 2 Drawing Sheets

(56) References Cited

U.S. PATENT DOCUMENTS

| | | | | |
|---|---|---|---|---|
| 6,021,678 A * | 2/2000 | Vardiman | ............ | G01N 1/2258 |
| | | | | 73/863.11 |
| 6,202,469 B1 * | 3/2001 | Nakamura | ......... | G01N 27/4077 |
| | | | | 73/114.73 |
| 7,685,894 B2 * | 3/2010 | Bruzzi | ................ | G01N 1/2247 |
| | | | | 73/864.33 |
| 7,739,898 B2 * | 6/2010 | Shaddock | ............... | F01N 13/08 |
| | | | | 73/23.31 |
| 7,739,924 B2 | 6/2010 | Nair | | |
| 8,087,307 B2 * | 1/2012 | Gauthier | .............. | G01N 1/2202 |
| | | | | 73/863.23 |
| 8,087,308 B2 * | 1/2012 | Gauthier | .............. | G01N 1/2258 |
| | | | | 73/863.23 |
| 8,464,573 B2 * | 6/2013 | Sekiya | ............... | G01N 27/4077 |
| | | | | 204/424 |
| 8,539,988 B2 * | 9/2013 | Guedon | ............. | G01N 35/1097 |
| | | | | 141/21 |
| 9,534,988 B2 * | 1/2017 | Karki | ....................... | F23N 5/003 |
| 2007/0277605 A1 * | 12/2007 | Fouts | .................. | G01D 11/245 |
| | | | | 73/431 |
| 2008/0229848 A1 * | 9/2008 | Bruzzi | ................ | G01N 1/2247 |
| | | | | 73/864.33 |
| 2012/0312074 A1 * | 12/2012 | Allmendinger | ...... | G01N 1/2252 |
| | | | | 73/23.31 |

FOREIGN PATENT DOCUMENTS

| | | |
|---|---|---|
| DE | 10019853 A1 | 10/2001 |
| DE | 102008000372 A1 | 8/2009 |
| DE | 102012217596 A1 | 3/2014 |
| WO | WO 9637771 A1 | 11/1996 |
| WO | WO 2012038128 A1 | 3/2012 |
| WO | WO 2012146417 A1 | 11/2012 |
| WO | WO 2012146422 A1 | 11/2012 |

* cited by examiner

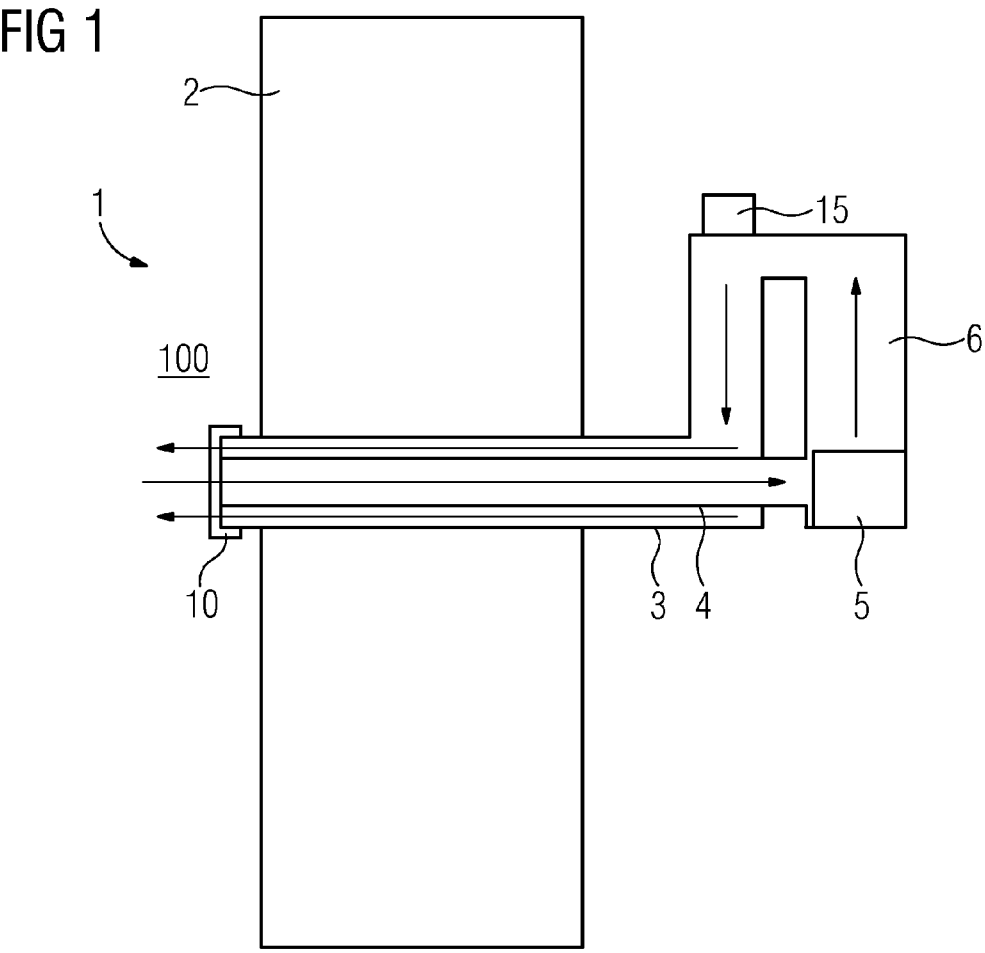
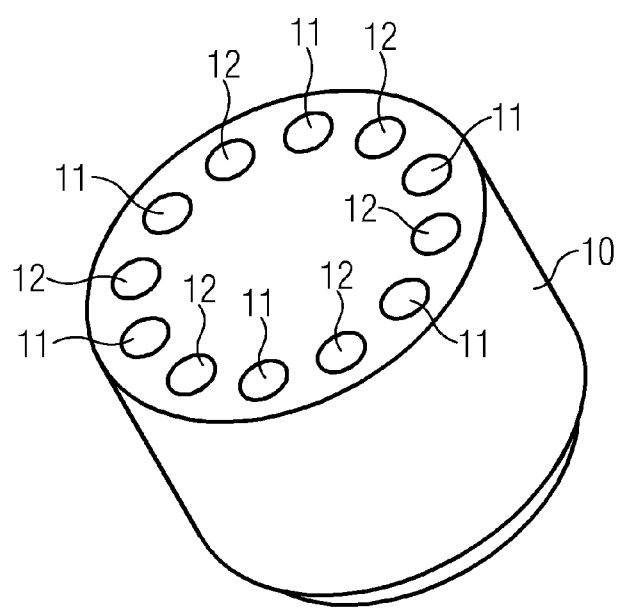

SENSOR APPARATUS FOR ANALYZING A GAS MIXTURE IN A PROCESS CHAMBER

CROSS-REFERENCE TO RELATED APPLICATIONS

This application claims priority to European Application No. DE 20 2014 005 420.7, having a filing date of Jul. 2, 2014, the entire contents of which are hereby incorporated by reference.

FIELD OF TECHNOLOGY

The following relates to a sensor apparatus for analyzing a gas mixture which is present in a process chamber.

BACKGROUND

During the operation of an industrial plant in which gases are generated or processed, the parameters of which, for example composition, temperature etc., it is necessary to monitor, corresponding gas sensors are used. Often, however, such gas sensors cannot be positioned directly at the measurement site since conditions unsuitable for the sensor, for example excessively high temperatures, prevail there. In order nevertheless to be able to determine the gas parameters, it is necessary to place the sensors at a suitable distance from the measurement site. The gas to be analyzed must in this case be fed from the measurement site to the gas sensor by means of a suitable feed line.

For example, in DE 10 2012 217 596, in order to measure corrosive conditions in a boiler of a thermal power station, sensor devices are used which comprise a gas feed through the boiler wall with an opening toward the interior of the boiler and a sensor chamber outside the boiler. A sensor element for detecting the stoichiometry of a combustion taking place in the boiler is arranged in the sensor chamber, in order to monitor the combustion inter alia so as to improve the energy efficiency and to limit the emissions. The sensor in the sensor chamber is accordingly arranged separated from the actual measurement site.

If the gas to be measured then lies in a region with a reduced pressure, or generally with varying pressure conditions, in order to ensure continuous and reliable monitoring the gas needs to be actively delivered from the measurement site to the sensor element. To this end, separate pumps are generally used, which extract a part of the gas from the measurement site and deliver it to the sensor element in the sensor chamber. However, such an external pump constitutes additional outlay for the overall system, and besides the corresponding additional costs the restricted operational reliability and the finite lifetime of the pump also have detrimental effects.

In order to overcome these disadvantages due to the use of the pump, the system may for example be operated without a pump, the gas diffusion which takes place anyway being used as a transport mechanism for the gas from the measurement site to the sensor element. A disadvantage which occurs in this case is that even small pressure differences between the gas feed and the gas discharge can cause the diffusive gas flow to be stopped or to be superimposed with an undesired flow.

SUMMARY

An aspect relates to a way of analyzing a gas in a process chamber, with which the aforementioned disadvantages in relation to the feed of the gas from the process chamber to the gas sensor are avoided. In particular, the intention is to ensure that the gas flows uniformly over the gas sensor during operation of the apparatus.

The sensor apparatus according to embodiments of the invention for analyzing a gas in a process chamber comprises a housing and a gas sensor for analyzing at least a part of the gas, the gas sensor being arranged at a determined position in the housing. It furthermore comprises a gas feed for connecting the housing to the process chamber in order to feed the part of the gas from the process chamber into the housing and to the determined position, and a gas discharge for discharging the gas from the housing. The gas feed and the gas discharge are configured as tubes lying inside one other.

The sensor apparatus furthermore comprises a closure cap at the combustion chamber-side end of the tubes lying inside one another. This closure cap in turn comprises an even number of at least four openings with the same area, which are connected alternately as a gas inlet and a gas outlet to the tubes lying inside one another.

Here, alternately means that the openings are essentially arranged in a linear shape, for example as a circle, square, rectangle or the like, and when moving along the line to an opening which constitutes a gas feed, this is followed by an opening which constitutes a gas discharge. Those openings which constitute a gas feed are connected to one of the tubes lying inside one another, while the openings which constitute a gas discharge are connected to the other of the tubes lying inside one another.

Embodiments of the invention are based on the discovery that, for example for a purely diffusive gas feed to the gas sensor, it is crucial for the pressure difference between all openings for the gas feed and openings for the gas discharge to be as small as possible. It has been discovered that a uniform arrangement of an equal number of openings respectively for the gas discharge and the gas feed at the smallest possible distance from one another advantageously leads to very small pressure differences between the gas feed and the gas discharge, even when conditions which are very detrimental—in terms of the gas feed—prevail in the combustion chamber, for example high flow speeds with a variable flow direction. A defined and reliable gas flow to the gas sensor is thus advantageously achieved even when there is only a low pumping power, or no pumping power at all.

Configurations and refinements of the sensor apparatus are, for example:

The sensor apparatus may have a device for generating a gas flow through the housing.

In particular, a heating apparatus for heating the gas in the housing in order to initiate thermal convection and a riser tube may be provided as a device for generating a gas flow, the riser tube being arranged in such a way that the part of the gas heated by the heating apparatus rises in the riser tube. The heating apparatus may be a heating device which is simultaneously used as a heater for the gas sensor. As an alternative or in addition, the heating apparatus may comprise a Peltier element. Such an element constitutes a heat source of small size. It is particularly advantageous for a down tube to be provided in the housing in addition to the riser tube, and for the Peltier element to be fitted in such a way that it displaces heat from the region of the down tube into the region of the riser tube.

As an alternative or in addition, the device for generating a gas flow may be an acoustic transducer, in particular a piezoelectric sonotrode. Besides the ultrasound oscillation per se, piezoelectric sonotrodes also generate an air flow directed away from the transducer, the so-called ultrasonic wind. They are small, robust and flexible in terms of the sound frequency and amplitude. Advantageously, the sonic transducer does not comprise any moving parts which could be perturbed by dirt, and is not subjected to substantial wear.

These devices are advantageously low-energy, small and low-maintenance, but—in comparison with a pump—they generate a small gas flow, and thus likewise profit from embodiments of the invention.

The openings in the closure cap may be circular, particularly in the form of bores.

The openings may be arranged in a circle. In this case, if the openings are distributed uniformly over the circumference of the circle, the arrangement is maximally symmetrical and therefore as far as possible independent of a flow direction of the gas in the process chamber.

There may be precisely 12 openings. In this way, the best possible compromise is achieved between outlay for production and uniform distribution of the openings, and therefore pressure stability.

An essentially cylindrical sleeve may be arranged between the closure cap and the tubes lying inside one another, which sleeve alternatingly has external slits and bores for alternate connection of the openings to the tubes lying inside one another.

The tubes lying inside one another may be arranged coaxially. In this way, in turn, the greatest possible symmetry of the arrangement is achieved.

The gas sensor may be a semiconductor-based gas sensor. These sensors are simple to produce, small and low-maintenance.

Embodiments of the invention are particularly suitable for a combustion chamber of a power station, which comprises a combustion chamber wall delimiting the combustion chamber and a sensor apparatus according to embodiments of the invention, wherein the gas feed and the gas discharge are arranged passing through the combustion chamber wall. For example, the sensor apparatus may be used in a heating boiler through which combustion gas flows, particularly of a fossil fuel-fired steam generator of a thermal power station, in order to measure a CO and/or $CO_2$ and/or $O_2$ concentration in the combustion gas.

In the context of embodiments of the present invention, the terms "vertical" and "horizontal" refer to a global coordinate system based on the effect of gravity. The same applies for terms such as "upward" and "downward".

BRIEF DESCRIPTION

Some of the embodiments will be described in detail, with reference to the following figures, wherein like designations denote like members, wherein:

FIG. 1 shows an embodiment of a sensor apparatus for analyzing gas from a combustion chamber;

FIG. 2 shows an embodiment of a closure cap with openings for the gas feed and gas discharge for the sensor apparatus;

DETAILED DESCRIPTION

Figure 3:
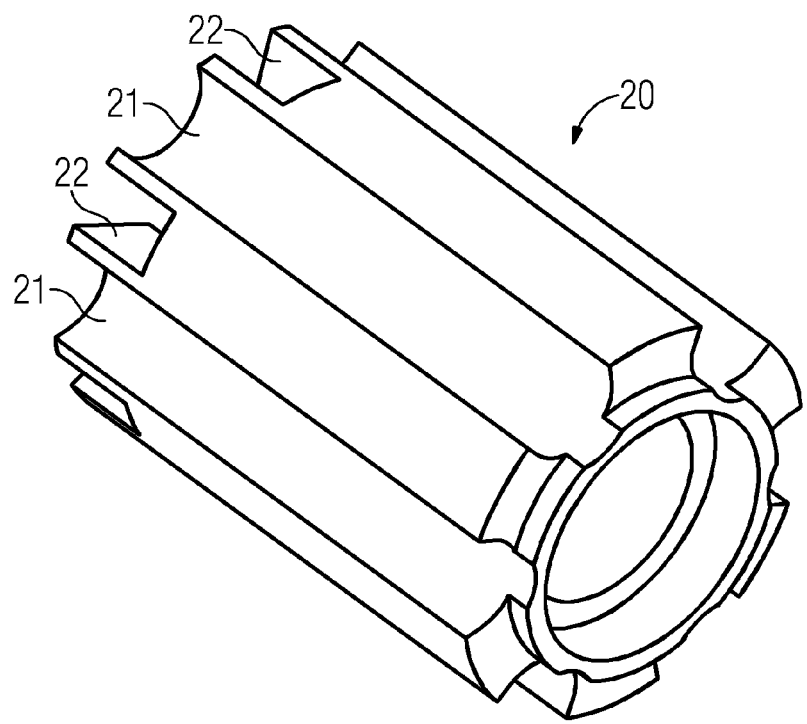
FIG. 3 shows an embodiment of a sleeve for alternate connection of the openings to tubes lying inside one another for gas feed and gas discharge.

The figures show aspects of an exemplary embodiment of embodiments of the invention in various views. References which are the same refer to elements which are the same. FIG. 1 shows a detail of a combustion chamber 1 in a thermal power station. The combustion chamber 1 comprises a combustion chamber wall 2 and gas 100, for example combustion gas, located in the combustion chamber. The detail according to FIG. 1 represents a side view.

A feed line 4 and a discharge line 3 pass through the combustion chamber wall 2. The two lines 3, 4 are used to guide a part of the gas 100 to a gas sensor 5, which is arranged outside the combustion chamber 1 since the harsh environment and the temperatures in the combustion chamber 1 do not allow operation of the gas sensor 5 in the combustion chamber 1. The feed line 4 and the discharge line 3 are arranged coaxially in the region of the combustion chamber wall 2, and the feed line 4 forms the inner part. It is also possible for the feed line 4 to be configured as the outer tube in the coaxial guide.

A particle filter, which is used to filter out coarse dirt particles, may be arranged in the feed line 4. Optionally after passing through the particle filter, the part of the gas which is taken into the feed line 4 flows past the gas sensor 5 itself. The gas sensor 5 and further components of the sensor apparatus are arranged in a housing outside the combustion chamber wall 2. The gas sensor 5 comprises one or more sensor elements for analyzing the part of the gas. The sensor elements may for example be high-temperature gas sensors, for example gallium oxide-based semiconductor gas sensors. The gas sensor 5 is connected to control electronics (not represented) for readout and evaluation of the sensor data.

After flowing past the gas sensor 5, the part of the gas is forwarded and enters a tube loop. In the present exemplary embodiment, it then flows past an ultrasound sonotrode 15. The latter generates a weak gas flow, i.e. it generates a slight pumping action.

The gas subsequently leaves the region of the sensor apparatus again through the discharge line 3 and re-enters the combustion chamber 1. Because of the coaxial arrangement of the feed line 4 and the discharge line 3, pressure differences between these tube openings are minimized. This is advantageous so that the suction action due to the sound is only influenced as little as possible by flows in the combustion chamber 1, or is entirely unaffected.

In a modified configuration, in addition to the sound, it is possible to use the thermal convection as a driving force for the gas flow. To this end, it is expedient to provide at least one riser tube. In other words, the part of the gas inside the housing should lie before a tube part rising in the operating state and in the flow direction of the gas. If the gas is heated in this region, then it experiences a force upward in the riser tube, which contributes to driving the gas flow. If the gas sensor 5 comprises, for example, heating elements which are in any case expedient for the operation of gallium oxide-based semiconductor gas sensors, then the gas sweeping over the gas sensor 5 is warmed by the heating of the gas sensor 5 and will move upward and therefore drive the gas flow.

In the present exemplary embodiment, the closure of the feed line 4 and of the discharge line 3 is formed by a closure cap 10, which is represented in FIG. 2. The closure cap 10 is cylindrical with a radius of 0.5 cm, one base surface being substantially open and another base surface being substantially closed. Twelve bores 11, 12 each with a radius of 0.5 mm are provided in the closed base surface. The twelve bores 11, 12 are arranged uniformly distributed on a circle with a radius of about 0.35 cm. Six of the bores 11 are configured for the feed line 4 and the remaining six of the bores 12 are configured for the discharge line 3. The bores 11 for the feed line alternate with the bores 12 for the discharge line.

Figure 4:
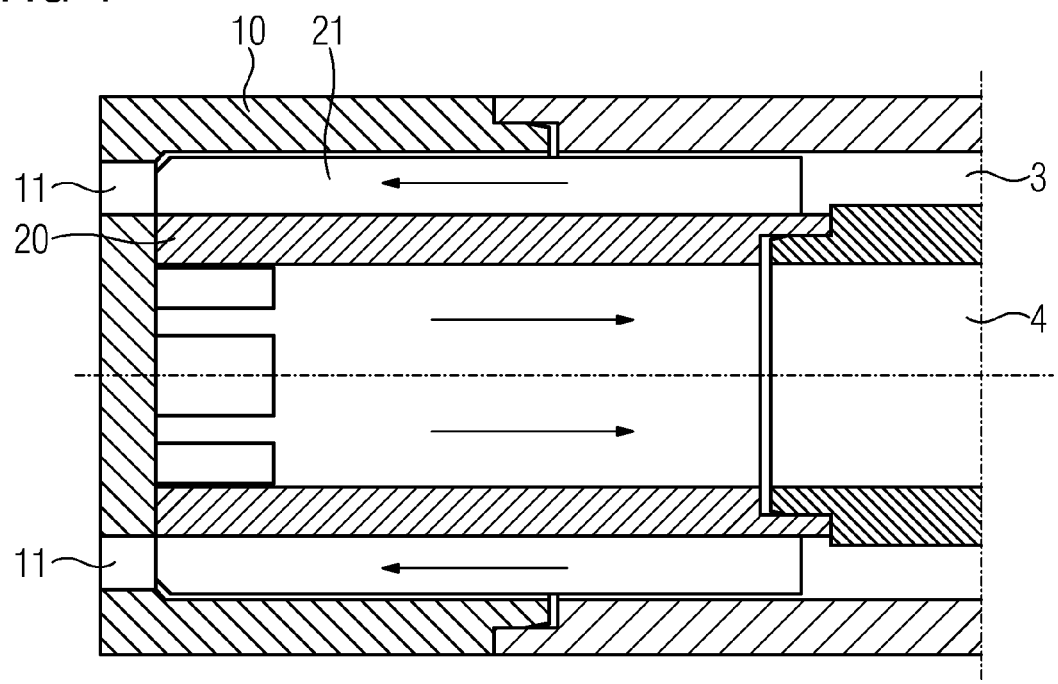
FIG. 4 shows a section through the combustion chamber-side end of an embodiment of the tubes lying inside one another.

Arranged between the coaxial feed line 4 and discharge line 3, on the one hand, and the closure cap 10 on the other hand, there is a sleeve 20 which is configured for the gas guidance between the bores 11, 12 and the coaxial feed line 4 and discharge line 3. FIG. 3 shows a perspective view of the sleeve 20, and FIG. 4 shows the arrangements of the elements with respect to one another in a sectional view. The sleeve 20 is in principle cylindrical. Slits 21 and bores 22 are arranged alternately on its lateral surface. In the assembled state with the closure cap 10 and feed line 4 and discharge line 3, the slits connect the discharge line 3—in this example the outer-lying tube—to the bores 12 for the gas outlet. The bores 22 of the sleeve 20, on the other hand, connect the feed line 4—in this example the inner-lying tube—to the bores 11 of the closure cap 10.

Expediently, the closure cap 10 and the sleeve 20 consist of a heat-resistant steel, for example steel 1.4841, in order to withstand the conditions in the combustion chamber. Owing to the very symmetrical arrangement of the bores 11, 12, pressure differences between the discharge line 3 and feed line 4 are minimized, and the closure cap and the corresponding tube system can be made very small, in particular with a diameter <12 mm.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A sensor apparatus for analyzing a gas in a process chamber, comprising:
    a housing;
    a gas sensor for analyzing at least a part of the gas, the gas sensor being arranged at a determined position in the housing;
    a gas feed for connecting the housing to the process chamber to feed the part of the gas from the process chamber into the housing and to the determined position;
    a gas discharge for discharging the gas from the housing, wherein the gas feed and the gas discharge are configured as tubes lying inside one another; and
    a closure cap at a combustion chamber-side end of the tubes lying inside one another, the closure cap comprising an even number of at least four openings with a same area, which are connected alternately as a gas inlet and a gas outlet to the tubes lying inside one another.

2. The sensor apparatus as claimed claim 1, wherein the at least four openings are circular.

3. The sensor apparatus as claimed in claim 1, wherein the at least four openings are arranged in a circle.

4. The sensor apparatus as claimed in claim 1, wherein the least four openings amounts to precisely twelve openings.

5. The sensor apparatus as claimed in claim 1, wherein a cylindrical sleeve is arranged between the closure cap and the tubes lying inside one another, the cylindrical sleeve alternatingly has external slits and bores for alternate connection of the at least four openings to the tubes lying inside one another.

6. The sensor apparatus as claimed in claim 1, wherein the tubes lying inside one another are arranged coaxially.

7. The sensor apparatus as claimed in claim 1, wherein the gas sensor is a semiconductor-based gas sensor.

8. A combustion chamber of a power station, comprising:
    a combustion chamber wall delimiting the combustion chamber; and
    a sensor apparatus as claimed in claim 1, wherein the gas feed and the gas discharge are arranged passing through the combustion chamber wall.

9. The sensor apparatus as claimed in claim 1, further comprising a device for generating a gas flow through the housing.

10. The sensor apparatus as claimed in claim 9, wherein the device for generating a gas flow is a heating device.

11. The sensor apparatus as claimed in claim 9, wherein the device for generating a gas flow is an acoustic transducer.

12. The sensor apparatus as claimed in claim 9, wherein the device for generating a gas flow is a piezoelectric sonotrode.

* * * * *